US005475227A

United States Patent [19]
LaRue

[11] Patent Number: 5,475,227
[45] Date of Patent: Dec. 12, 1995

[54] HYBRID PHOTOMULTIPLIER TUBE WITH ION DEFLECTOR

[75] Inventor: Ross A. LaRue, Santa Clara County, Calif.

[73] Assignee: Intevac, Inc., Santa Clara, Calif.

[21] Appl. No.: 345,246

[22] Filed: Nov. 28, 1994

Related U.S. Application Data

[63] Continuation-in-part of Ser. No. 91,764, Jul. 14, 1993, Pat. No. 5,374,826, which is a continuation-in-part of Ser. No. 992,430, Dec. 17, 1992, Pat. No. 5,326,978.

[51] Int. Cl.⁶ ..................................................... H01J 31/30
[52] U.S. Cl. ............................ 250/397; 250/207; 313/532
[58] Field of Search ..................................... 250/397, 207, 250/214 VT; 313/532

[56] References Cited

U.S. PATENT DOCUMENTS

| | | | |
|---|---|---|---|
| 3,885,178 | 5/1975 | Goehner | 313/1 |
| 5,326,978 | 7/1994 | Aebi et al. | 250/397 |
| 5,374,826 | 12/1994 | LaRue et al. | 250/397 |

OTHER PUBLICATIONS

L. K. vanGeest et al, "Hybrid Phototube with Si Target", SPIE, vol. 1449, Elec. Image Tubes & Image Inten. II, 1991, pp. 121–134.

K. C. Schmidt et al, "Con. Channel Elect. Mult. Op. in the Pulse Saturated Mode", IEEE Trans. Nucl. Sci., Jun. 1966, pp. 100–111.

J. P. Edgecumbe et al, "A GaAsP Photocathode with 40% QE at 515nm", SPIE, vol. 1655, Elect. Tubes and Image Inten., Feb. 1992.

K. A. Costello et al, "Transferred Elect. Photocathode with Greater Than 5% Quan. Eff. Beyond One Micron", SPIE, vol. 1449, Elect. Tubes and Image Intensifiers II, 1991.

*Primary Examiner*—Jack J. Berman
*Assistant Examiner*—Kiet T. Nguyen
*Attorney, Agent, or Firm*—Stanley Z. Cole

[57] ABSTRACT

A focused electron/bombarded hybrid photomultiplier tube comprising a photocathode, focusing electrodes, and a collection anode disposed in a detector body. The collector anode includes a diode for receiving the focused output electron beam from the photocathode. The current gain between the photocathode output current and the detector output signal from the diode is over 1000 at a tube operating voltage of 7 kV. The noise factor has been determined to be 1.1. A hybrid photomultiplier tube includes a photocathode, a photodiode for collecting and multiplying electrons emitted by the photocathode and providing an output signal and electrodes for focusing the electrons on the photodiode. A vacuum envelope encloses a vacuum region between photocathode and the detector. A conductor disposed on or adjacent to a sidewall of the vacuum envelope reduces the effect of electrical charges on the inside wall of the vacuum envelope on the trajectories of the electrons. An ion deflector electrode is disposed adjacent to the photodiode anode and extends photocathode operational life and improves noise factor.

24 Claims, 8 Drawing Sheets

HYBRID PHOTOMULTIPLIER TUBE WITH ION DEFLECTOR

CROSS REFERENCE TO RELATED APPLICATION

This application is a continuation-in-part of Ser. No. 08/091,764, filed Jul. 14, 1993, which in turn is a continuation-in-part of Ser. No. 07/992,430, filed Dec. 17, 1992 now U.S. Pat. No. 5,326,978.

FIELD OF THE INVENTION

This invention relates to hybrid photomultiplier tubes which have an electron bombarded photodiode as a collection anode and the means for reducing or eliminating the deleterious effects of ion feedback on cathode life as well as detector electrical performance.

BACKGROUND OF THE INVENTION

Conventional photomultiplier tubes include a vacuum envelope containing a photocathode, several dynodes and an electron collector. Light entering the tube through a window and incident on the photocathode causes electrons to be emitted by the photocathode. The electrons impinge on the successive dynodes, causing electron multiplication by secondary emission. After impingement on the last dynode, the electrons are collected and delivered on an output lead of the tube to provide an output signal which is representative of the input light.

A hybrid photomultiplier tube includes a photocathode, electron focusing electrodes and an electron bombarded photodiode anode. Electrons emitted by the photocathode are focused onto the photodiode. The electrons penetrate into the photodiode material and create electron-hole pairs, causing a multiplication effect. Gain is produced by the photodiode rather than the dynodes, as in the conventional photomultiplier tube.

A hybrid photomultiplier is disclosed by L. K. van Geest et al in "Hybrid Phototube With Si Target", SPIE, Vol. 1449, Electron Image Tubes and Image Intensifiers, II, 1991, pages 121–134. A photomultiplier tube using both dynodes and an impact ionization diode for electron multiplication is disclosed in U.S. Pat. No. 3,885,178 issued May 20, 1975 to Goehner.

A bias voltage on the order of 10 kilovolts is typically applied between the anode and cathode of a hybrid photomultiplier tube. The electrons are accelerated by the applied field and bombard the photodiode anode, which results in multiplication gain. However, electron bombardment at the photodiode surface can generate positive ions due to surface contamination resulting from intermediate processing steps as well as mobile cesium atoms on the diode surface due to cathode and tube body cesiation. In particular, tube body cesiation just prior to cathode installation or seal is a necessary requirement to extend cathode life and tube operation and hence there is a concomitant contamination of the diode surface by cesium. The contamination of the diode surface can be positively ionized by energetic photoelectrons striking the surface. These ions are then accelerated by the applied tube bias of 10 kilovolts in a direction opposite to the photoelectrons, by the positive nature of their charge, and hence toward the light sensitive photocathode. These accelerated positive ions strike the photocathode surface and damage the enabling cesium oxide layer formed during the photocathode cesiation process or the underlying photocathode material resulting in reduced operational life of the photocathode. In addition, positive ions striking the photocathode surface results in a pulse of electrons emitted into the vacuum envelope which are accelerated to and multiplied at the photodiode anode. This results in random output pulses at the anode proportional in average number per unit time interval to the incoming light intensity on the photocathode. Therefore detector noise performance is also degraded.

One prior art approach to eliminate the deleterious effects of ion feedback in vacuum tubes is the ion trap which usually consists of one or more electrodes placed near the collecting anode and the application of positive bias on these electrodes. The geometry of these ion trap electrodes is designed not to interfere with the electron trajectories or orbits throughout the vacuum tube and therefore the general performance of the vacuum tube. The application of sufficient positive bias to the ion trap electrodes can divert or trap positive ions generated at the anode by incoming energetic electrons. The positive ions are therefore deterred or prevented from entering the bulk of the vacuum tube where they can be accelerated and damage or degrade other vacuum tube components including the cathode. A significant difficulty with this approach is related to the required positive bias of the ion trap which requires one or more additional electrical feedthroughs through the vacuum envelope to access the ion trap electrodes. Furthermore, many vacuum tubes operate with one polarity bias supply, usually negative for grounded anode configuration; however, the inclusion of an ion trap as described requires a positive bias and therefore a bipolar power supply to operate the vacuum tube properly. This adds to the expense and difficulty of operating the device.

SUMMARY OF THE INVENTION

A hybrid photomultiplier tube in accordance with the present invention comprises a photocathode for emitting electrons in response to incident photons, a detector for collecting and multiplying the electrons emitted by the photocathode and providing an output signal representative of the incident photons, an electron optical structure for controlling the trajectories of the electrons between the photocathode and the detector, means for accelerating the electrons between the photocathode and the detector, a vacuum envelope enclosing a vacuum region between the photocathode and the detector, a conductor disposed on or adjacent to at least a portion of the vacuum envelope for reducing the effect of electrical charges on the vacuum envelope on the trajectories of the electrons, and a relatively smaller grounded electrode of appropriate geometry placed near the photodiode anode which provides ion optical means for deflecting positive ions generated near the photodiode away from the photocathode. The electron optical structure may, for example, typically comprise first and second focusing electrodes.

The grounded electrode placed near the photodiode which provides the ion optical means will henceforth be referred to as the ion deflector or ion deflector electrode. This electrode is not circularly symmetric as are all other structures in the presently described preferred embodiment and comprises a semicircular shell or cylinder of appropriate length mounted perpendicularly to the photodiode surface with the center of the semicircle coinciding with that of the photodiode. Metal tabs located at the base of the half cylinder provide a means of brazing, welding or spot welding the ion deflector in place to the metal of the circularly symmetric photodiode header anode. The photodiode header is part of the collecting anode and is therefore held at ground potential along with the ion deflector electrode which is brazed, welded or spot welded to the header.

The photocathode is typically located on an inside surface of a window in the vacuum envelope. The photocathode preferably comprises a group III-V semiconductor material, such as gallium arsenide, gallium arsenide phosphide, indium phosphide or indium phosphide/indium gallium arsenide; however, the photocathode may also comprise a traditional photocathode, such as, the alkali-antimonides ($Na_2KSb:Cs$, $Cs_3Sb$, or $Na_2KSb$, etc.).

The vacuum envelope preferably includes a coaxial feedthrough for coupling the output signal externally of the vacuum envelope. The photodiode preferably comprises an avalanche photodiode mounted on a header the center conductor of which is the coaxial feedthrough.

According to another aspect of the invention there is provided an improved vacuum tube of a hybrid photomultiplier tube including a vacuum envelope, a charged particle source within the vacuum envelope for emitting charged particles, and optics for controlling the trajectories of the charged particles within the vacuum envelope. The improvement comprises a conductor of appropriate geometry disposed adjacent to a collecting anode at ground potential which provides the ion optics means to deflect positively generated ions away from sensitive components of the vacuum tube prone to damage by energetic positive ions.

BRIEF DESCRIPTION OF THE DRAWINGS

For a better understanding of the present invention, reference is made to the accompanying drawings, which are incorporated herein by reference and in which.

DETAILED DESCRIPTION OF THE PREFERRED EMBODIMENTS

Figure 1A:
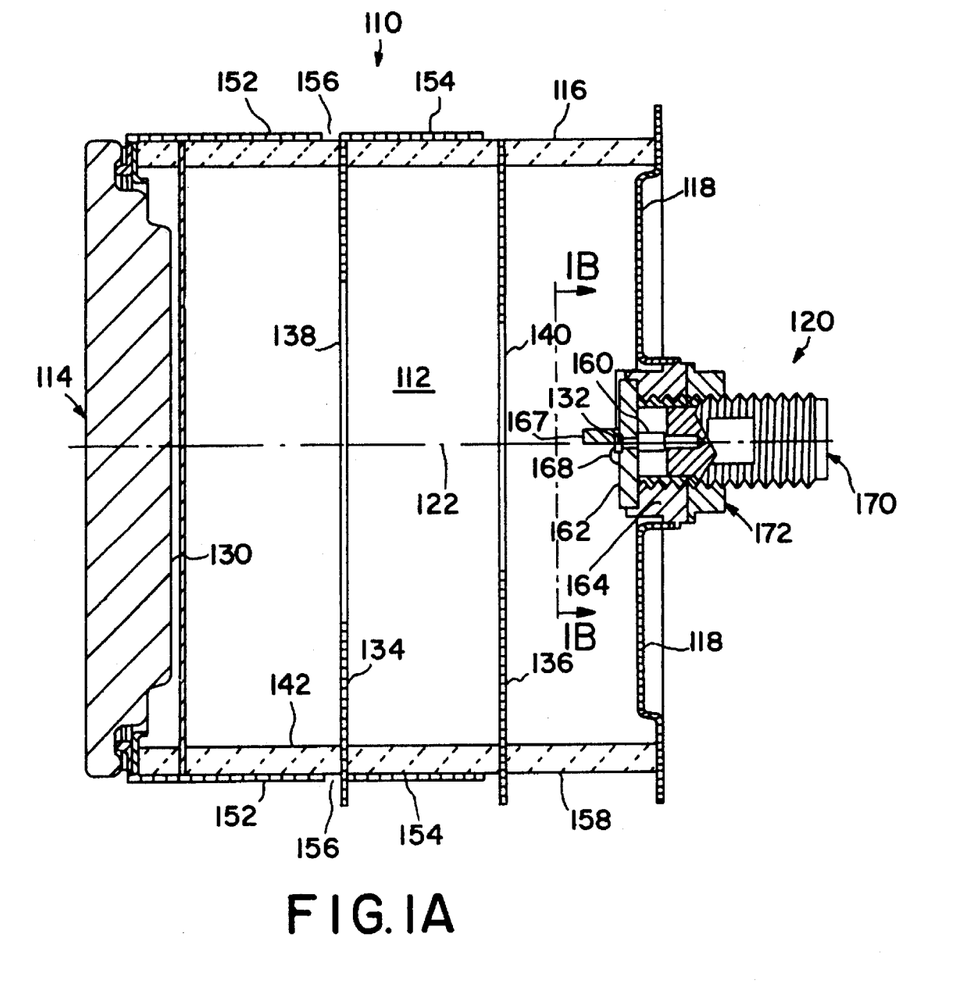
FIG. 1A is a cross-sectional view of a hybrid photomultiplier tube with the ion deflector electrode.
Figure 1B:
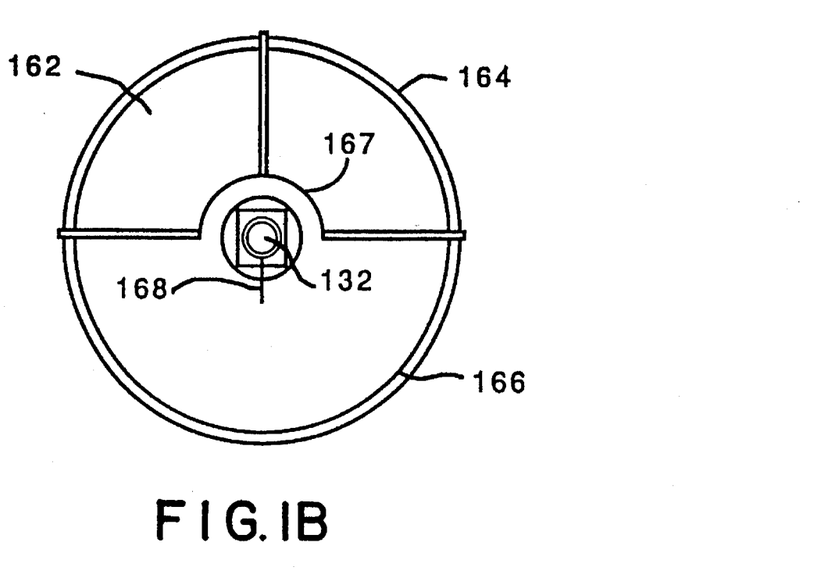
FIG. 1B is a top view of the collection anode taken along line 1B of FIG. 1A.
Figure 2:
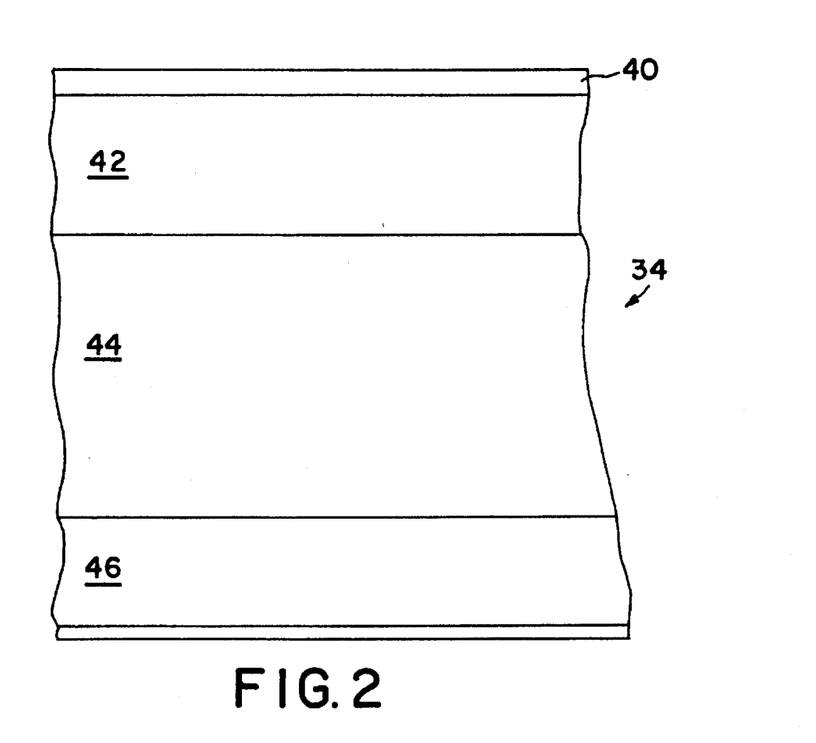
FIG. 2 is a detailed view of the diode element of the hybrid photomultiplier tube.

A hybrid photomultiplier detector is shown in FIGS. 1A, 1B and 2. A standard GaAs, GaAsP or other III-V photocathode 130 is mounted at one end of a cylindrical detector body 110. In the embodiment shown in FIG. 1, detector body 110 is comprised of a series of ceramic rings stacked to give the appropriate dimensions. Alternatively, the detector body could be formed as a specially designed cylinder or in any other shape dictated by the application.

Two electron focusing rings 134 and 136 are disposed in detector body 110. In the embodiment shown in FIG. 1A, rings 134 and 136 are mounted between pairs of the ceramic rings comprising detector body 110. Other means of attaching the focusing rings may be used without departing from the invention. Rings 134 and 136 connect to an external power source (not shown) via suitable conductors. The purpose of focusing rings 134 and 136 is to concentrate and direct the photoelectrons generated by the photocathode onto the collecting anode, as shown schematically in FIG. 3.

A collection anode 120 is disposed at the far end of detector body 110. Anode 120 comprises a broadband microwave connector 170, a step-tapered coaxial transmission line section 160, and a solid state diode 132 terminating the transmission line. In a preferred embodiment, diode 132 is an AlGaAs/GaAs pin diode optimized for electron bombardment current gain. As shown in more detail in FIG. 2, the preferred embodiment of diode 34 comprises three separate layers 40, 42 and 44 formed on an n+ GaAs substrate 46. The top layer 40 is doped to be a p-type $Al_{30}Ga_{70}As$ layer approximately 250 Angstroms thick. Layer 40 provides a potential barrier near the surface of the diode to keep generated electron minority carriers from recombining at the surface. The composition of layer 40 is also chosen for stability and for its resistance to oxidation during processing in air. Layer 42 is doped to be p-type GaAs approximately 0.25 microns thick.

Layer 44 is undoped GaAs and is approximately 10 microns thick. The thickness of layer 44 is chosen to optimize the response time of the diode according to the following principles:

The transit time Ttransit of an electron across an undoped layer of thickness w is $$T\text{transit} = w/V_{sat}$$

where $V_{sat}$ is $1\times10^7$ cm/sec. The RC time constant $T_{RC}$ of the loaded diode is $$T_{RC} = \epsilon(\pi r^2/W)R_L$$

where r is the radius of the diode and $R_L$ is the diode load (50W, for example). The time response of the loaded diode is minimized when $T_{transit} = T_{RC}$ or, $$w/V_{sat} = \epsilon(\pi r^2/w)R_L$$

The optimum w or undoped thickness is therefore $$w = \sqrt{\epsilon \pi r^2 V_{sat} R_L}$$

The optimum time response is therefore $$T_{opt} = \sqrt{\epsilon \pi r^2 R_L/V_{sat}}$$

Since $T_{opt}$ is proportional to diode radius, the time response of the hybrid photomultiplier detector using such a diode is greatly improved over detectors which do not focus.

A preferred embodiment of a hybrid photomultiplier tube is shown in FIG. 1. Equipotential lines and electron and ion trajectories of the hybrid photomultiplier tube are shown in the schematic diagram of FIG. 3. A vacuum envelope 110, or housing, encloses a vacuum region 112, typically having a pressure on the order of $10^{-10}$ torr. The vacuum envelope 110 includes a window 114, a sidewall 116, an electrode 118 and a connector assembly 120. The sidewall 116 typically comprises several ceramic rings. The vacuum envelope 110 typically has circular symmetry about a central axis 122 such that the sidewall 116 is cylindrical. However, the vacuum envelope 110 may have other physical configurations.

A photocathode 130 is located on the inside surface of window 114. The photocathode 130 is preferably a group III-V semiconductor material, such as gallium arsenide, gallium arsenide phosphide, indium phosphide or indium phosphide/indium gallium arsenide. A suitable gallium arsenide phosphide photocathode is disclosed by J. P. Edgecumbe et al in "A GaAsP Photocathode With 40% QE at 515 nm", SPIE Vol. 1655, Electron Tubes and Image Intensifiers, February 1992. A suitable gallium arsenide photocathode is disclosed by K. A. Costello et al in "Imaging GaAs Vacuum Photodiode with 40% Quantum Efficiency at 530 nm", SPIE Vol. 1243, Electron Image Tubes and Image Intensifiers, 1990. Another suitable photocathode is disclosed by K. Costello et al in "Transferred Electron Photocathode with Greater Than 5% Quantum Efficiency Beyond One Micron", SPIE Vol. 1449, Electron Tubes and Image Intensifiers II, 1991. Typically, a wafer including layers of epitaxially grown, suitable photocathode material is bonded to window 114, and the wafer substrate is etched away in the case of GaAs or GaAsP photocathodes. In the case of a transferred electron photocathode, the substrate may be left intact or removed. The photocathode 130 emits electrons in response to incident light received through window 114.

The electrons emitted by photocathode 130 are focused on a photodiode 132 by electrodes 134 and 136 sealed within the vacuum envelope 110. The electrodes 134 and 136 have central apertures 138 and 140, respectively, for passage of the electrons to photodiode 132. The placement and dimensions of the electrodes 134 and 136 are selected to focus electrons emitted by photocathode on photodiode 132. Additional focusing electrodes can be used, if desired.

Photocathode 130 is typically biased at about −10 Kv. At this photocathode voltage, electrode 134 is typically biased at −9878 volts, and electrode 136 is biased at −9700 volts. Electrode 118 is electrically connected to photodiode 132 and is grounded. The bias voltages are supplied by suitable voltage sources (not shown).

The photodiode 132 is preferably an avalanche photodiode and is mounted on axis 122. The photodiode 132 is selected to produce electron multiplication when impacted by energetic electrons from photocathode 130. In a preferred embodiment, the photodiode 132 is a GaAs/AlGaAs avalanche photodiode. Other suitable photodiodes include PIN photodiodes, as shown in FIG. 2.

Figure 3:
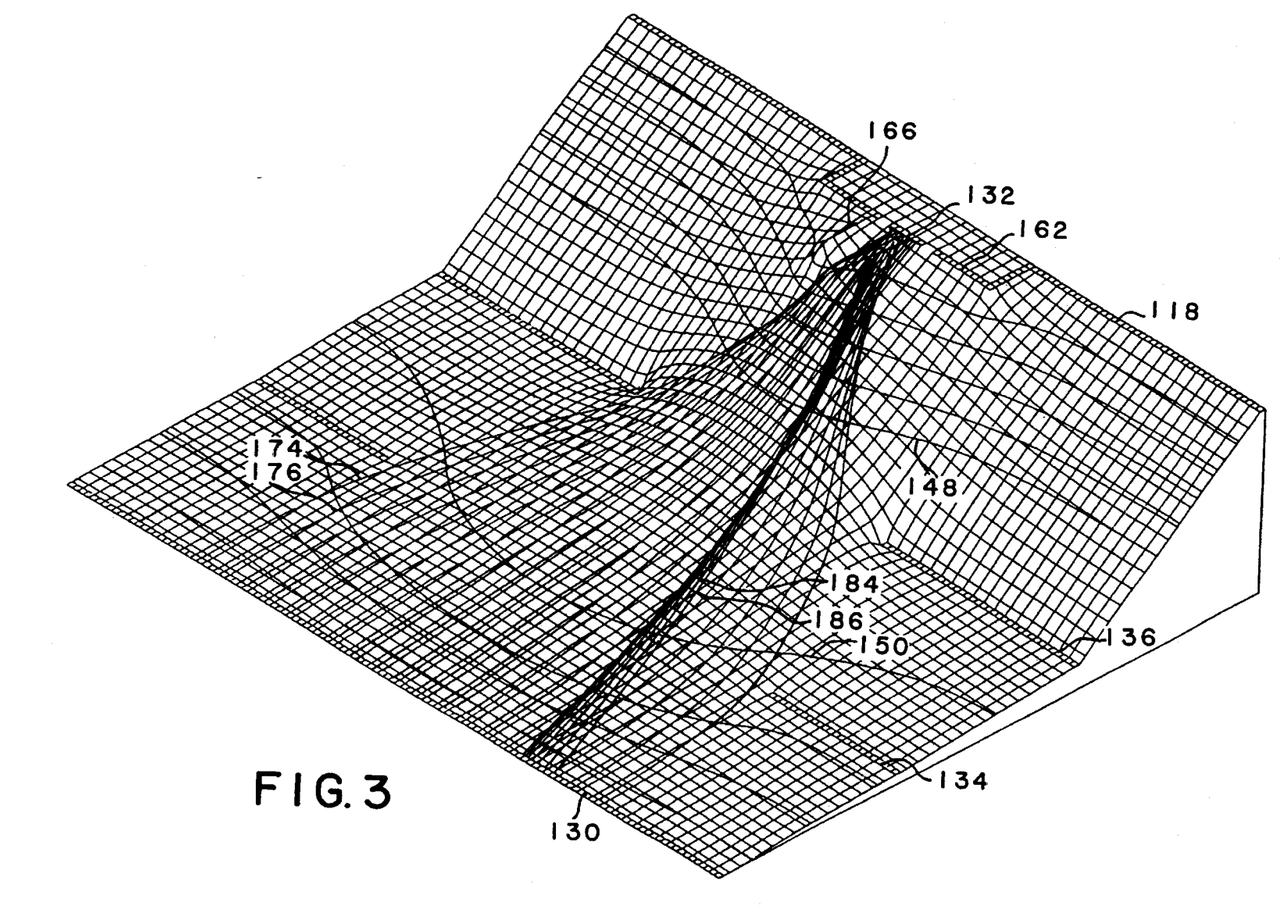
FIG. 3 is a three dimensional simulation plot showing the operation of the hybrid photomultiplier tube. Both photoelectron and feedback ion trajectories are plotted. The magnitude of the electrical potential within the tube is in the vertical direction.

As noted above, electrical charges may build up on an inside surface 142 of sidewall 116. The sidewall 116 may, for example, be a ceramic material having a thickness on the order of about 0.065 inch. As shown in FIG. 3, electrons emitted from photocathode 130 are focused by electrodes 134 and 136 along trajectories 174, 176, etc. that are incident on photodiode 132. Equipotential lines 148, 150, etc. are established by the electrode configuration. When electrical charge builds up on the inside surface 142 of FIG. 1, the field configuration and, hence, the electron trajectories 174, 176 of FIG. 3 may be affected such that the electrons are no longer focused on photodiode 132.

To overcome this problem, a conductor is located on or adjacent to sidewall 116 of vacuum envelope 110. In the embodiment of FIG. 1, the conductor includes conductors 152 and 154 on an outside surface of sidewall 116. The conductor 152 is electrically connected to photocathode 130, and the conductor 154 is electrically connected to electrode 134. A gap 156 is provided between conductors 152 and 154 to prevent photocathode 130 from being short circuited to electrode 134. In the above example, the gap 156 can be relatively small, since the voltage difference between electrode 134 and photocathode 130 is on the order of 100 volts.

The effect of the conductors 152 and 154 is believed to be as follows. The charges on inside surface 142 of sidewall 116, believed to be positive electrical charges, are passivated by electrical charges of equal magnitude and opposite polarity on conductors 152 and 154. This causes electrical fields resulting from the charges on inside surface 142 to be confined to the regions between the inner and outer surfaces of sidewall 116. The charges on the inner and outer surfaces of sidewall 116 effectively form a capacitor, and minimal fringing electric fields extend from these charges into the vacuum region 112 between photocathode 130 and photodiode 132. As a result, the electrical charges on inside surface 142 do not appreciably affect the electron trajectories 174, 176, etc. followed by electrons between photocathode 130 and photodiode 132.

The connector assembly 120 includes a center conductor 160, mounted in a ceramic insulator 162. The ceramic insulator 162 is supported by an outer conductor 164. The ceramic insulator 162 is brazed to the center conductor 160 and to the outer conductor 164. The outer conductor 164 is welded to electrode 118 to form a vacuum tight assembly. Photodiode 132 is mounted on the end of center conductor 160 that extends into vacuum region 112 so as to substantially cover the center conductor 160. The ceramic insulator 162 includes a surface metallization 166, shown in FIG. 1B, which is electrically connected to electrode 118, and which surrounds but does not contact the center conductor 160. A thin wire 168 is connected between metallization 166 (shown in FIG. 1A and 1B) and the top contact pad of photodiode 132. The connector assembly 120 further includes a conventional SMA-type coaxial connector 170 secured to center conductor 160 and outer conductor 164 by a lock nut 172.

The connector assembly 120 has several advantages in the operation of the hybrid photomultiplier tube. The connector functions as a portion of the vacuum envelope 110 and thus affects the shape of the electric fields within the tube. The internal surface of the connector is exposed to the open volume of the tube so that the surface can be electron scrubbed during tube processing, resulting in a cleaner tube. The connector supports photodiode 132 on center conductor 160 which is completely covered by the photodiode 132.

Thus, the bias voltage applied to the photodiode 132 does not affect the electric fields which focus electrons onto the photodiode. The preferred photodiode 132 has a relatively low operating voltage, thus permitting use of an industry-standard SMA output connector. The connector is impedance matched to 50 ohms to permit a flat frequency response well beyond 1 GHz.

In a preferred embodiment, the ion deflector electrode 167 (shown in FIGS. 1A and 1B) is mounted on the ceramic insulator 162 of the connector assembly 120. This is accomplished by brazing, welding or spot welding metal tabs at the base of the ion deflector electrode to the outer conductor 164. The length of the ion deflector is chosen short enough not to interfere with the electron trajectories and focus but long enough to give sufficient lateral velocity to low energy positive ions leaving the photodiode area.

Figure 4A:
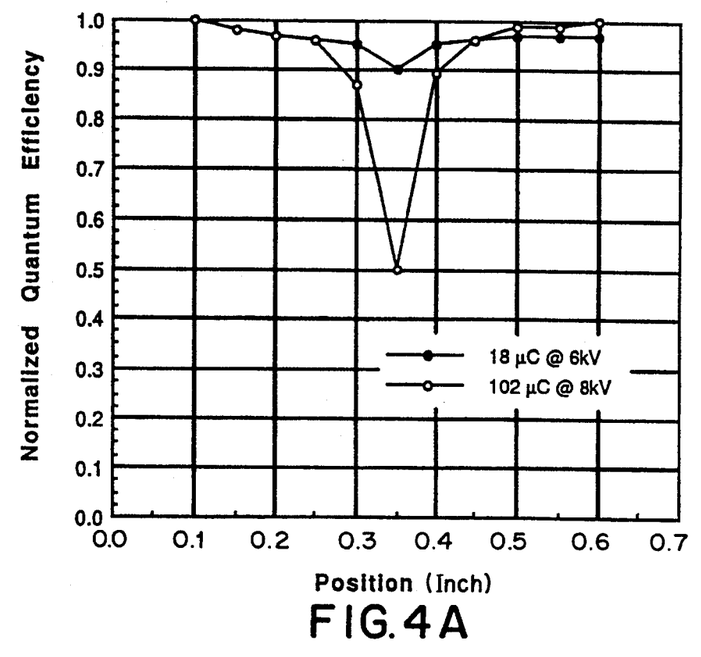
FIG. 4A is the actual measured quantum efficiency versus cathode position of a hybrid photomultiplier tube with no ion deflector after 0.102 mC of cathode operation. The dip in the center is due to ion feedback damage.
Figure 4B:
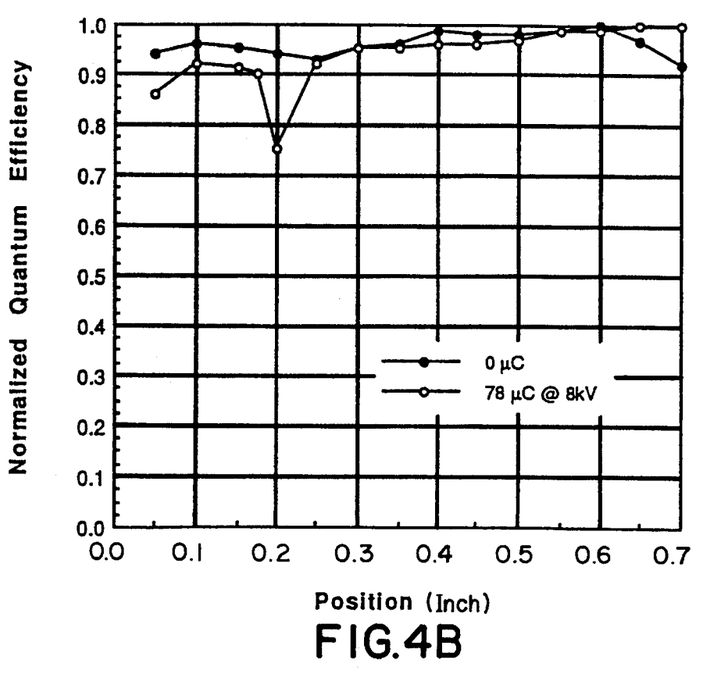
FIG. 4B is the actual measured quantum efficiency versus cathode position of a hybrid photomultiplier tube with an ion deflector after 0.078 mC of cathode operation. The dip is now shifted to the left due to the ion optics of the ion deflector electrode.
Figure 5A:
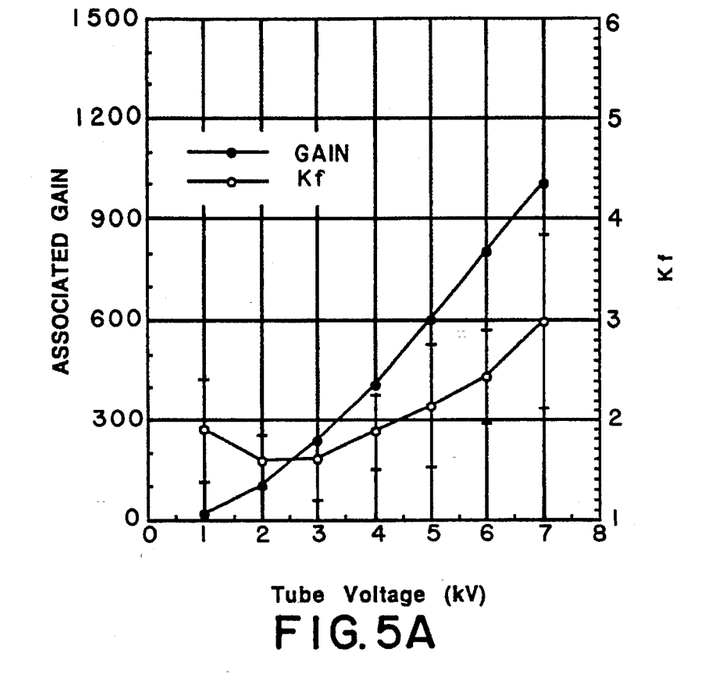
FIG. 5A is an actual plot of gain and noise factor of a hybrid photomultiplier tube with no ion deflector.
Figure 5B:
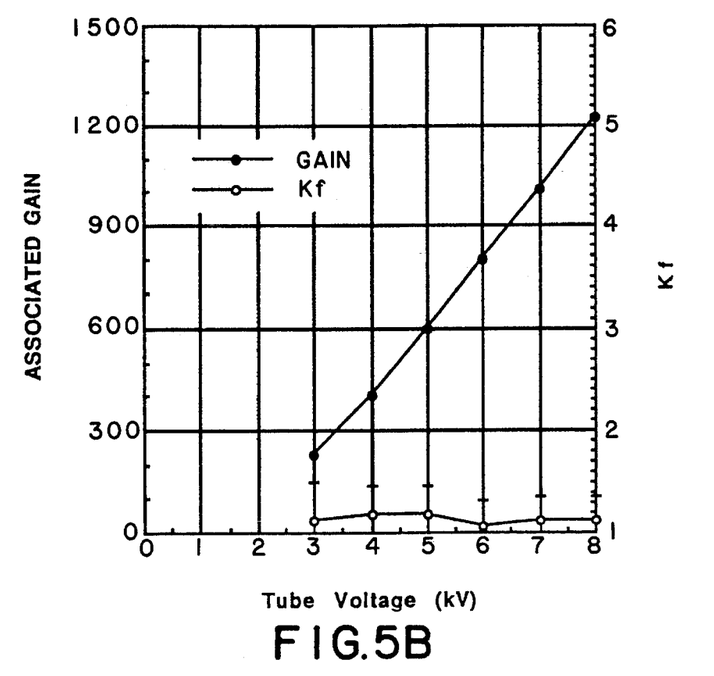
FIG. 5B is an actual plot of gain and noise factor of a hybrid photomultiplier tube with an ion deflector. The noise factor in this figure is approximately 1.1.

This is possible because as shown in FIG. 3 the accelerating electric field is highest near the photodiode anode since the largest voltage drop is between the second baffle closest to the anode. Therefore photoelectrons approaching the ion deflector electrode have achieved a sufficient momentum so that their trajectories are not greatly perturbed by the asymmetry in the electric field caused by the ion deflector electrode. The asymmetry or lateral component of electric field near the photodiode is caused by the shape of the ion deflector electrode which is semicircular and tends to shield the diode from the voltage applied to the second baffle closest to the anode on one side only. The positive ions generated near the diode on the other hand start out with little or no momentum since electrons cannot impart significant momentum to a stationary atom during the ionization process. Therefore positive ions initially move along the gradient of the potential which is upward and to one side. As the ions continue to drift back toward the front of the tube they travel in a straight line but at a sufficient angle off axis, 122 (FIG. 1A), to the hybrid photomultiplier detector. Sufficient off axis angle is achieved when the accelerated ions traveling back to the front of the hybrid photomultiplier miss the active area of the photocathode thus protecting the photocathode and resulting in improved noise performance of the detector. This discussion of the function of the ion deflector electrode is illustrated in the simulation plot of FIG. 3 which shows the photoelectron trajectories 174 and 176 etc., from the photocathode 130, converging on the target photodiode 132. Positive ions generated at the photodiode come back to the photocathode, accelerated by the tube bias, but at an angle off axis to the tube. In this case the ion trajectories 184 and 186 etc., are not deflected completely off an 18 mm. photocathode. The grid spacing in FIG. 3 is 0.5 mm. Hybrid photomultiplier tubes were fabricated with and without the ion deflector electrode. The tubes were operated so that the photocathode emitted 0.102 mC and 0.078 mC of total charge, respectively. A point source was then scanned across the photocathode of each tube and the photocathode current and quantum efficiency as a function of cathode position was determined. These plots are shown in FIG. 4A for tube 13002 with no ion deflector and FIG. 4B for tube 13009 with an ion deflector. Note the dip in quantum efficiency which indicates ion feedback damage has been shifted to the left for the tube with the ion deflector. In this case the ions have not been completely deflected off the 18 mm. photocathode. Another ion deflector tube was fabricated but with a 5 mm. diameter GaAs photocathode centered on the axis of the tube body. The gain and noise factor of this tube, 01, versus tube voltage was measured and compared with tube 10C86 which had no ion deflector. These results are plotted in FIGS. 5A and 5B. Note the gain of each tube is the same but the noise factor of the tube with the ion deflector is dramatically reduced to approximately 1.1. This indicates that feedback ions are now missing the photocathode due to its smaller diameter. The noise factor of 1.1 is comparable or better than commercially available photomultiplier tubes which utilize a dynode chain.

Figure 6A:
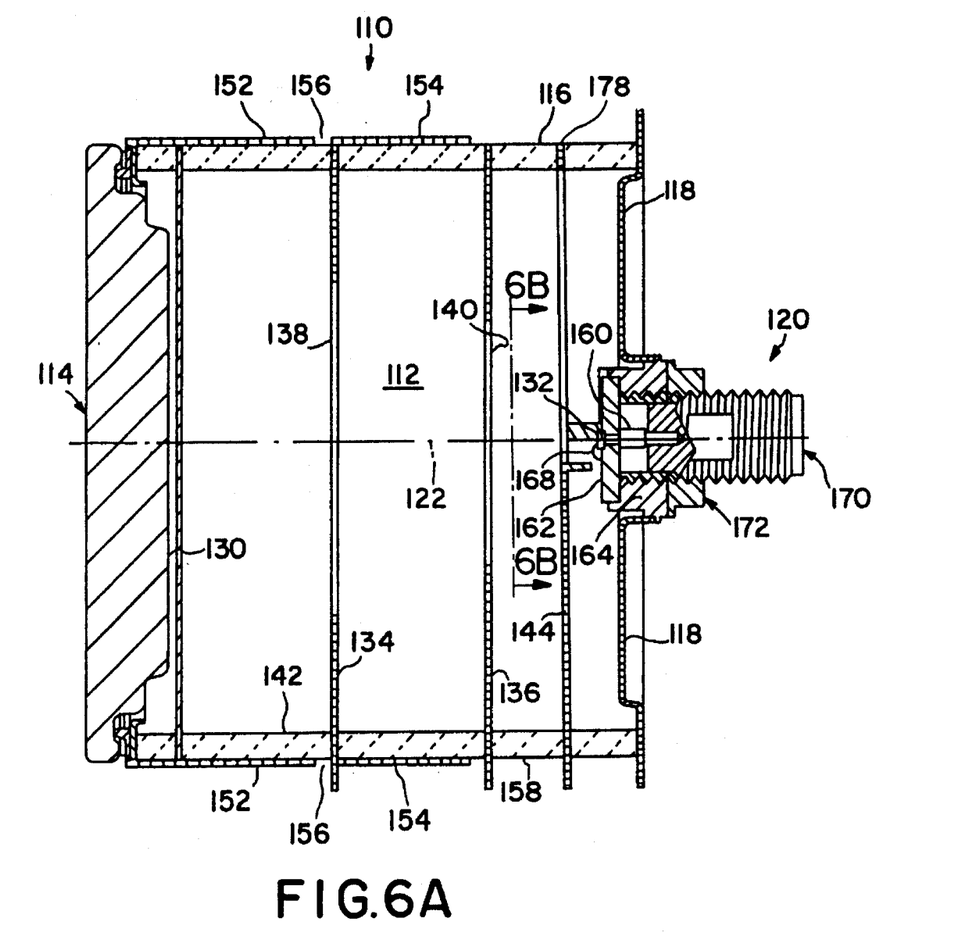
FIG. 6A is a detailed drawing of an alternate embodiment which includes the counter electrode 144 which increases the lateral electrostatic field just above the photodiode.
Figure 6B:
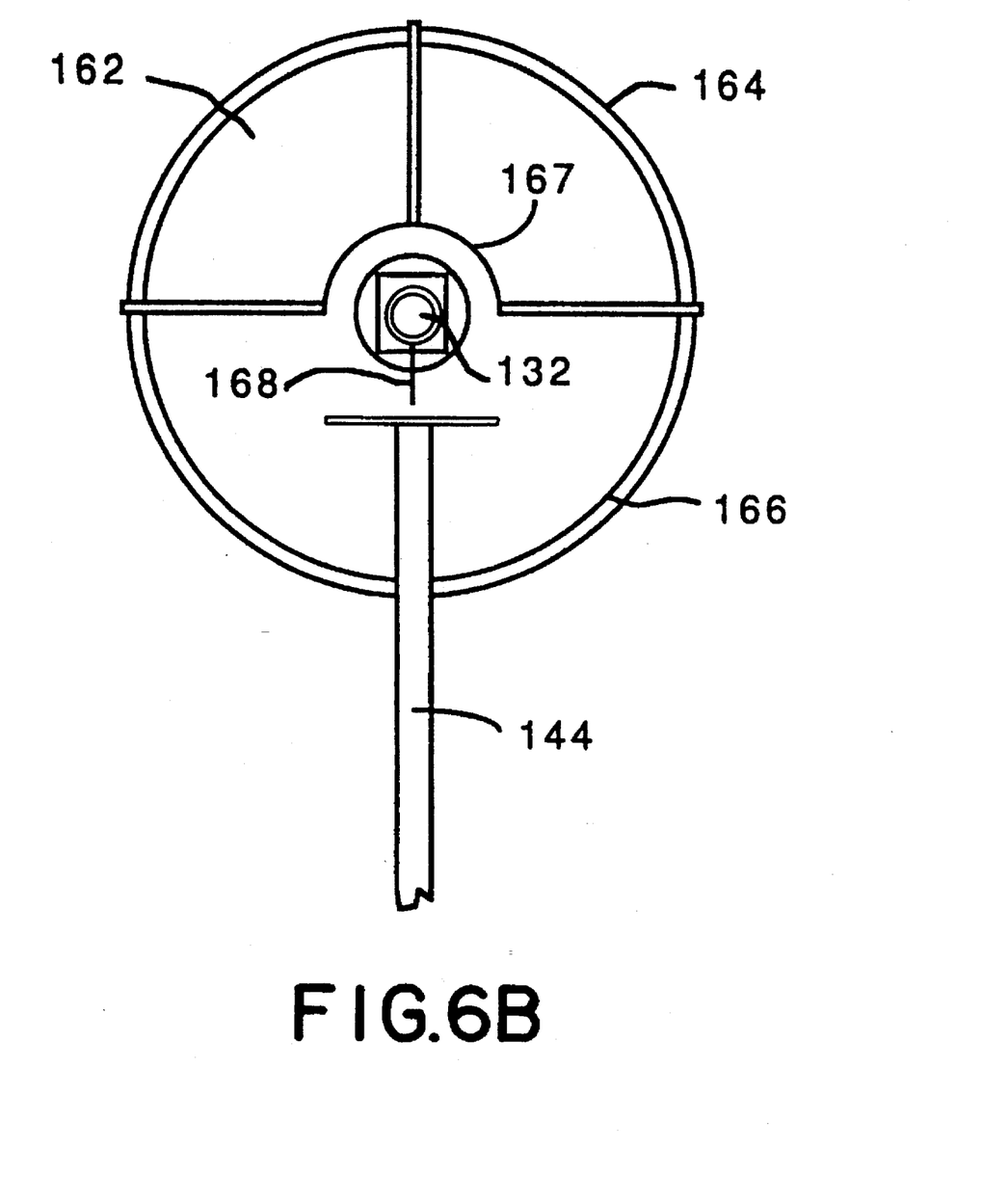
FIG. 6B is a top view of the photodiode header area of the alternate embodiment which shows the position of the ion deflector and counter electrode relative to the photodiode; and, FIG. 7 is an alternate embodiment three dimensional simulation plot of the hybrid photomultiplier tube with an ion deflector and negatively biased counter electrode to increase the lateral electric field. This combination deflects the positive ions even more.
Figure 7:
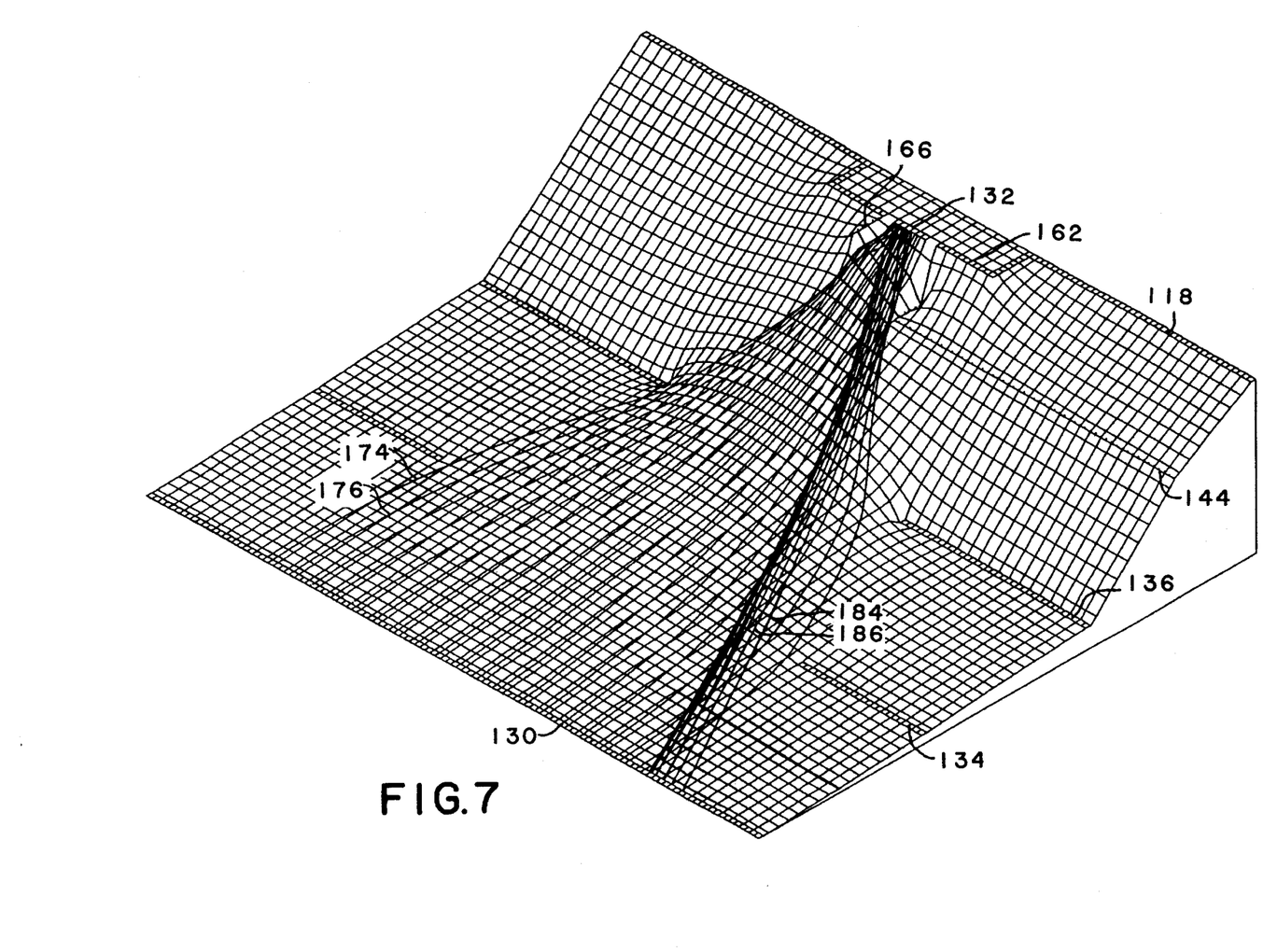

In the alternate embodiment shown in FIGS. 6A and 6B a negatively biased counter electrode increases the lateral field between the ion deflector electrode 167, and the counter electrode, 144. In the simulation plot of FIG. 7 the cathode, 130, focus ring electrode, 134, focus ring electrode, 136, and the counter electrode 144, are biased to −10 kV, −9.45 kV, −8.7 kV and −3 kV, respectively. Now the positive ions generated at the photodiode, 132, completely miss the photocathode which has a diameter of 18 mm. The counter electrode may consist of a wire connected at one end to a tube body ring electrode 178 of FIG. 6A for connection to a negative bias and connected at the other end to a flattened section bent at a right angle which faces the ion deflector electrode 167. The geometry and bias of the counter electrode 144, and in particular the length, position and bias of the wire section is chosen to perturb the electrostatic field lines as little as possible in the bulk of the hybrid photomultiplier tube. This is accomplished by computing a constant electrostatic potential contour such as 148 of FIG. 3 at the bias of the counter electrode but without the counter electrode in place and then positioning and shaping the wire section along this contour. This will ensure that the counter electrode will not modify the electron trajectories sufficiently to miss the target photodiode.

The use of an ion deflector at the same electrical potential as the collecting anode to limit the detrimental effects of ion feedback on sensitive tube components has been described thus far in connection with a hybrid photomultiplier tube. In fact this technique, i.e., control, via the ion optics of the ion deflector electrode, of the trajectories of feedback ions, can be utilized, more generally, in other vacuum tubes which include a vacuum envelope, a charged particle source and optics for controlling the trajectories of the charged particles within the vacuum envelope. The geometry of the ion deflector is chosen to have little or no perturbing effect on the trajectories of the charged particles from the charged particle source and requires no separate bias for operation other than the anode bias.

While there have been shown and described what are at present considered the preferred embodiments of the invention, it will be obvious to those skilled in the art that various changes and modifications may be made therein without departing from the scope of the invention as defined by the appended claims.

What is claimed is:

1. A hybrid photomultiplier tube comprising:

a photocathode for emitting electrons in response to incident photons;

a detector for collecting and multiplying said electrons impinging thereon and providing an output signal representative of said incident photons;

at least one electrode for focusing said electrons on said detector;

a vacuum envelope defining a vacuum region between said photocathode and said detector; and a relatively smaller electrode compared to said detector positioned at said detector for deflecting positive ions.

2. A hybrid photomultiplier tube in accordance with claim 1 in which said detector comprises a photodiode.

3. A hybrid photomultiplier tube in accordance with claim 2 in which said relatively smaller electrode is mounted perpendicular to the photodiode surface.

4. A hybrid photomultiplier tube in accordance with claim 1 in which said smaller electrode is electrically connected to said detector.

5. A hybrid photomultiplier tube in accordance with claim 1 in which said smaller electrode is held at ground potential.

6. A hybrid photomultiplier tube in accordance with claim 1 wherein said vacuum envelope includes a window and said photocathode is located on an inside surface of said window.

7. A hybrid photomultiplier tube in accordance with claim 6 wherein said photocathode comprises a group III-V semiconductor material.

8. A hybrid photomultiplier tube in accordance with claim 6 wherein said photocathode is selected from a group consisting of GaAs, GaAsP, InP and InP/InGaAs.

9. A hybrid photomultiplier tube in accordance with claim 1 wherein said at least one electrode comprises first and second spaced-apart electrodes having apertures for passing said electrons.

10. A hybrid photomultiplier tube in accordance with claim 1 wherein said detector comprises an avalanche photodiode.

11. A hybrid photomultiplier tube in accordance with claim 10 wherein said vacuum envelope includes a coaxial feedthrough connected to said photodiode, said coaxial feedthrough coupling said output signal externally of said vacuum envelope.

12. A hybrid photomultiplier tube in accordance with claim 11 wherein said coaxial feedthrough includes a center conductor and wherein said photodiode is mounted on said center conductor.

13. A hybrid photomultiplier tube in accordance with claim 12 wherein said photodiode covers an end of said center conductor.

14. A hybrid photomultiplier tube including a vacuum envelope, a charged particle source within said vacuum envelope for emitting charged particles, optics for controlling trajectories of said charged particles being positioned within said vacuum envelope, and a collecting anode within said vacuum envelope for collecting and multiplying said charged particles, the improvement comprising:

a conductor disposed within said vacuum envelope adjacent to said collecting anode and maintained at substantially the same electrical potential of said collecting anode for providing ion optic means to deflect positively generated ions.

15. A hybrid photomultiplier tube in accordance with claim 14 wherein said charged particle source comprises a group III-V semiconductor material.

16. A hybrid photomultiplier tube in accordance with claim 14 wherein said conductor deflects said positively generated ions from sensitive components of said vacuum tube.

17. A hybrid photomultiplier tube in accordance with claim 14 in which said vacuum envelope includes a sidewall including means to reduce the effect of electrical charges on said sidewall on said trajectories of said charged particles within said vacuum.

18. A hybrid photomultiplier tube comprising:

a photocathode for emitting electrons in response to incident photons;

a photodiode for collecting and multiplying said electrons and providing an output signal representative of said incident photons;

electron optical input means for controlling the trajectories of said electrons between said photocathode and said photodiode;

means for applying an electric field between said photocathode and said photodiode for accelerating said electrons between said photocathode and said photodiode;

a vacuum envelope defining a vacuum region between said photocathode and said photodiode;

a conductor disposed on at least a portion of an outside surface of said vacuum envelope for reducing the effect of electrical charges on said vacuum envelope on the trajectories of said electrons; and an ion deflector electrode placed near said photodiode for reducing the deleterious effects of ion damage to said photocathode and improving noise performance of said hybrid photomultiplier tube.

19. A hybrid photomultiplier tube in accordance with claim 18 wherein said means for applying an electric field between said photocathode and said photodiode comprises first and second focusing electrodes.

20. A hybrid photomultiplier tube in accordance with claim 19 wherein said conductor on said envelope comprises a first conductive coating formed on said vacuum envelope which is electrically connected to said photocathode and a second conductive coating formed on said vacuum envelope which is electrically connected to said first focusing electrode, said first and second conductive coatings being spaced apart by a gap.

21. A hybrid photomultiplier tube as defined in claim 18 wherein said vacuum envelope includes a window and said photocathode is located on an inside surface of said window.

22. A hybrid photomultiplier tube as defined in claim 21 wherein said photocathode comprises a group III-V semiconductor material.

23. A hybrid photomultiplier tube as defined in claim 18 wherein said vacuum envelope includes a coaxial feedthrough for coupling said output signal externally of said vacuum envelope and wherein said photodiode is mounted on a center conductor of said coaxial feedthrough.

24. A hybrid photomultiplier tube as defined in claim 18 wherein said ion deflector electrode is adjacent to a negatively biased counter electrode to increase the lateral field just above said photodiode to deflect ions.

* * * * *